United States Patent
Buehring et al.

(10) Patent No.: US 8,071,814 B2
(45) Date of Patent: Dec. 6, 2011

(54) PROCESS FOR PREPARING POLYETHERAMINES

(75) Inventors: Dirk Buehring, Burghausen (DE); Andreas Gallas, Erlbach (DE); Klaus Raab, Burgkirchen (DE); Franz-Xaver Scherl, Burgkirchen (DE); Olaf Wachsen, Garching (DE)

(73) Assignee: Clariant Finance (BVI) Limited, Tortola (VG)

( * ) Notice: Subject to any disclaimer, the term of this patent is extended or adjusted under 35 U.S.C. 154(b) by 111 days.

(21) Appl. No.: 12/517,506

(22) PCT Filed: Jul. 7, 2007

(86) PCT No.: PCT/EP2007/006037
§ 371 (c)(1),
(2), (4) Date: Jun. 3, 2009

(87) PCT Pub. No.: WO2008/067857
PCT Pub. Date: Jun. 12, 2008

(65) Prior Publication Data
US 2010/0069671 A1    Mar. 18, 2010

(30) Foreign Application Priority Data
Dec. 6, 2006  (DE) .......................... 10 2006 057 457

(51) Int. Cl.
*C07C 209/16*    (2006.01)
(52) U.S. Cl. .......................... 564/480; 564/474; 564/479
(58) Field of Classification Search .................. None
See application file for complete search history.

(56) References Cited

U.S. PATENT DOCUMENTS

| | | | | |
|---|---|---|---|---|
| 4,014,933 A | * | 3/1977 | Boettger et al. | 564/447 |
| 4,618,717 A | | 10/1986 | Renken et al. | |
| 4,622,428 A | * | 11/1986 | Merger et al. | 564/480 |
| 4,760,190 A | * | 7/1988 | Twigg | 564/480 |
| 4,766,245 A | | 8/1988 | Larkin et al. | |
| 4,960,942 A | * | 10/1990 | Gerkin et al. | 564/479 |
| 5,003,107 A | | 3/1991 | Zimmerman et al. | |
| 5,331,101 A | * | 7/1994 | Habermann | 564/480 |
| 5,352,835 A | | 10/1994 | Dai et al. | |
| 5,530,127 A | | 6/1996 | Reif et al. | |
| 6,191,310 B1 | * | 2/2001 | Knifton et al. | 564/479 |
| 6,376,713 B1 | * | 4/2002 | Baiker et al. | 564/479 |
| 6,462,236 B2 | * | 10/2002 | Liang et al. | 564/336 |
| 7,183,438 B2 | | 2/2007 | Gerlach et al. | |
| 7,696,385 B2 | * | 4/2010 | Buehring et al. | 564/474 |
| 2003/0139289 A1 | | 7/2003 | Renken et al. | |

FOREIGN PATENT DOCUMENTS

| | | |
|---|---|---|
| DE | 1570542 | 7/1969 |
| DE | 1953263 | 2/1972 |
| DE | 1643426 | 3/1972 |
| DE | 3608716 | 12/1986 |
| DE | 4428004 | 2/1996 |
| DE | 10211101 | 9/2003 |
| DE | 102005029932 | 1/2007 |
| EP | 0436235 | 7/1991 |
| GB | 1185239 | 3/1970 |
| GB | 1319495 | * 6/1973 |
| GB | 2175910 | 12/1986 |
| WO | WO2007/000236 | 1/2007 |

OTHER PUBLICATIONS

International Search Report for PCT/EP2007/008037, mail dated Jan. 14, 2008.

* cited by examiner

*Primary Examiner* — Brian J Davis
(74) *Attorney, Agent, or Firm* — Tod A. Waldrop

(57) ABSTRACT

The invention provides a process for preparing polyetheramines of the formula (1), $R^2(NR^1R^3)_n$, in which n is a number from 1 to 20, $R^2$ represents an organic radical that contains between 2 and 600 oxalkylene groups, and $R^1$ and $R^3$ are alike or different and represent hydrogen or an organic radical having 1 to 400 carbon atoms, by combining a compound of the formula (2), $H(NR^1R^3)$, with a compound of the formula (3), $R^2(OH)_n$, in the presence of hydrogen with a metal-containing catalyst whose metal content, based on the dry, reduced catalyst excluding any support material that may be present, is composed either of at least 80% by mass of cobalt or, in the case of Raney catalysts, of at least 80% by mass of metals from the group consisting of cobalt and aluminium, the catalyst containing less than 5% by mass of copper.

16 Claims, No Drawings

PROCESS FOR PREPARING POLYETHERAMINES

The present invention relates to a process for preparing polyetheramines using cobalt catalysts.

Polyetheramines contain at least one polyalkylene glycol group, which crucially influences their properties. A high proportion of polyethylene glycol units gives rise to water-soluble polyetheramines, and a high proportion of polypropylene glycol units to water-insoluble polyetheramines. Moreover, the change in the molar masses of the polyalkylene glycols allows melting point and viscosity of the polyetheramines to be influenced. By virtue of the selection of suitable starter alcohols for the alkoxylation, it is possible to achieve surfactant properties. Moreover, it is possible with polyhydric alcohols to form branched polyetheramines which then lead, after aminolysis, to polyfunctional amines. This gives rise to various means of influencing the properties of a polyetheramine based thereon in a controlled manner by the selection of suitable polyalkylene glycols.

The prior art discloses various processes for preparing polyetheramines.

DE-A-16 43 426 describes a process for preparing polyoxyalkyleneamines proceeding from the corresponding alcohols using a nickel-copper-chromium catalyst which contains 60-85 mol % of nickel, 14-37 mol % of copper and 1-5 mol % of chromium.

U.S. Pat. No. 4,618,717 describes a process for preparing primary amines proceeding from oxyethylene glycol monoalkyl ethers using a catalyst which contains 50-90% by weight of nickel, 10-15% by weight of copper and 0.5-5% by weight of the elements chromium, iron, titanium, thorium, zirconium, manganese, magnesium or zinc.

U.S. Pat. No. 5,352,835 describes a supported catalyst for aminolysis, which is used for the conversion of polyoxyalkylene glycols to the corresponding amines. In this case, the catalyst consists of 15-30% by weight of nickel, 3-20% by weight of copper, 0.5-1% by weight of molybdenum and at least 50% by weight of γ-aluminum oxide, which serves as the support material.

U.S. Pat. No. 4,766,245 describes a process for preparing polyoxyalkylene-polyamines proceeding from the corresponding alcohols using a Raney nickel/aluminum catalyst which consists of nickel to an extent of 60-75% and of aluminum to an extent of 40-25%.

DE-A-36 08 716 describes a process for preparing polyoxyalkylenepoly-amines proceeding from the corresponding alcohols using a Raney nickel or Raney nickel/aluminum catalyst which additionally also contains 0.2-5% molybdenum.

U.S. Pat. No. 5,003,107 describes a process for reductive amination of polyoxytretramethylene glycols using a catalyst which contains 70-75% by weight of nickel, 20-25% by weight of copper, 0.5-5% by weight of chromium and 1-5% by weight of molybdenum.

DE-A-44 28 004 describes a process for preparing amines proceeding from alcohols, in which the catalyst contains 20-85% Zr, 1-30% Cu, 30-70% Ni, 0.1-5% Mo, 0-10% aluminum and/or manganese, in each case calculated as the oxide.

US-A-2003/0139289 describes an improved process for preparing amines proceeding from alcohols, aldehydes or ketones by means of a catalyst which, as well as nickel, copper and chromium, also comprises tin.

DE-A-19 53 263 describes a process for preparing amines proceeding from alcohols by means of a catalyst. The metal content of the catalyst consists of Co and Ni to an extent of 70 to 95% and of copper to an extent of 5 to 30%. In this catalyst, the weight ratio of Co to Ni ranges from 4:1 to 1:4.

DE-A-102 11 101 describes a process for preparing amines proceeding from alcohols or aldehydes, in which the catalyst contains 22-40% Zr, 1-30% Cu, 15-50% Ni, 15-50% Co, calculated in each case as the oxides.

DE-A-15 70 542 discloses a process for preparing polyetheramines, characterized in that polyethers of the formula I or II $$HO-R-(OR)_n-OH \qquad (I)$$

$$Z[(OR)_n-OH]_m \qquad (II)$$

in which R is an aliphatic radical having 2-4 carbon atoms, Z is a divalent to hexavalent aliphatic, araliphatic, aromatic or alicyclic radical which may be interrupted once or more than once by ether or amino groups, carbonamide, urethane or urea groups, n is integers from 1 to 50 and m=2 to 6 according to the valency of Z, in the presence of water and hydrogen over a hydrogenation-dehydrogenation catalyst consisting mainly of an element of the 8th transition group is reacted with ammonia at 200-280° C., preferably 220-250° C., under pressure.

It has now been found that, surprisingly, polyetheramines or polyoxyalkyleneamines, especially primary polyetheramines or polyoxyalkyleneamines, can be prepared from the corresponding alcohols and ammonia or amines (in the presence of hydrogen) at high conversions and selectivities by using a heterogeneous catalyst whose metal content, based on the dry, reduced catalyst excluding any support material present, either consists of cobalt to an extent of at least 80% by mass or consists of metals from the group of cobalt and aluminum to an extent of at least 80% by mass, and which comprises less than 5% by mass of copper.

It is possible here to use either support catalysts which, apart from the catalytically active metal content, also comprise support material, and metal catalysts without additional support material, for example the so-called "Raney catalysts".

The process is suitable both for continuous and batchwise preparation of polyetheramines.

The invention thus provides a process for preparing polyetheramines of the formula I $$R^2(NR^1R^3)_n \qquad (I)$$

in which n is from 1 to 20, $R^2$ is an organic radical which comprises between 2 and 600 oxyalkylene groups, and $R^1$ and $R^3$ are the same or different and are each hydrogen or an organic radical having from 1 to 400 carbon atoms, by combining a compound of the formula 2

(2)

with a compound of the formula 3

$$R^2(OH)_n \qquad (3)$$

in the presence of hydrogen with a catalyst which is metallic and whose metal content, based on the dry, reduced catalyst excluding any support material present, either consists of cobalt to an extent of at least 80% by mass or, in the case of the Raney catalysts, consists of metals from the group of cobalt and aluminum to an extent of at least 80% by mass, and which contains less than 5% by mass of copper.

The catalyst used for the process according to the invention contains, based on the dry, reduced catalyst excluding any support material present, either preferably at least 85% by mass, more particularly at least 90% by mass, especially at least 95% by mass of cobalt, or, for the Raney catalysts, preferably at least 85% by mass, more particularly at least 90% by mass, especially 95% by mass of metals from the group comprising cobalt and aluminum. For the Raney catalysts it is preferred that the cobalt content is higher than the aluminum content.

The catalyst may, as well as cobalt or cobalt and aluminum, also comprise minor proportions of other metals, such as nickel, chromium, iron, thorium, manganese, molybdenum, zinc, lithium and/or tin. These proportions, based on the dry, reduced catalyst excluding any support material present, are less than 20% by mass, preferably less than 15% by mass, more particularly less than 10% by mass and especially less than 5% by mass.

It has been found that a low copper content of the catalyst is advantageous especially in the preparation of primary polyetheramines. This applies to Raney catalysts and to supported catalysts. The copper content of the catalyst, based on the dry, reduced catalyst excluding any support material present, should therefore be less than 5% by mass, preferably less than 4% by mass, more particularly less than 2% by mass, especially between 1% by mass and 0.1% by mass. In a particularly preferred embodiment, catalysts having copper contents, where the copper content is based on the dry, reduced catalyst excluding any support material present, of less than 5% by mass, preferably less than 4% by mass, more particularly less than 2% by mass, especially between 1% by mass and 0.1% by mass, are used for the preparation of primary polyetheramines in which $R^1$ and $R^3$ are both hydrogen and in which n is one or is two.

The catalyst may be a supported catalyst or an unsupported catalyst.

When the catalyst is unsupported, it is preferably a catalyst of the Raney catalyst type. In the dry state, Raney catalysts, as are used in the process according to the invention, essentially consist of cobalt and aluminum, the sum of cobalt content and aluminum content for use in the process according to the invention being at least 80% by mass, preferably at least 85% by mass, more particularly at least 90% by mass, especially at least 95% by mass, based on the metal content of the dry catalyst. Due to their pyrophoric properties, Raney catalysts are often stored under water, and the removal of the water under a protective gas before using them in preparing polyetheramines is usually advantageous. In the case of pulverulent Raney catalysts, the average particle size may for example be between 20 and 200 micrometers. In the case of fixed bed Raney catalysts, the external shape may for example be irregular, spherical or hollow spherical with dimensions in the range from 1 to 6 mm. Amongst the Raney catalysts the hollow spherical Raney catalysts are preferred because of their high porosity. In the anhydrous, activated state the Raney catalysts preferably consist of from 40 to 99% by mass of cobalt and from 60 to 1% by mass of aluminum, more particularly from 55 to 98% by mass of cobalt and from 45 to 2% by mass of aluminum.

When the catalyst is supported, the catalyst may have any geometric shape, for example the shape of spheres, tablets, rods or cylinders in a regular or irregular version. The dimensions of the supported catalyst for fixed bed reactors are generally between 1 and 8 mm.

Supported catalysts in powder form have particle sizes of usually less than 200 micrometers and are used in stirred reactors or loop reactors, for example.

Suitable supports are the known support materials such as aluminum oxide, silica, amorphous silicon dioxide, kieselguhr, aluminosilicates, silicates, titanium dioxide, titanates, zirconium oxide, magnesium oxide, calcium oxide, mixtures of the aforementioned oxides, silicon carbide and activated carbon. Particularly suitable supports of this type are those having a specific surface area of from 50 to 300 m²/g (measured by the BET method) and a mean pore radius of from 5 nm to 200 nm (measured by mercury porosimetry), in particular aluminum oxide, amorphous silicon dioxide, silica, kieselguhr ($SiO_2$) and $SiO_2$—$Al_2O_3$ mixtures. Macroporous supports having a large pore radius between 10 nm and 100 nm are preferred, especially those comprising aluminum oxide as support material.

The supported catalysts are preferably used in the process according to the invention in the reduced and hence activated state. The supported catalysts of the process according to the invention consist of cobalt to an extent of at least 80% by mass, preferably to an extent of at least 85% by mass, more particularly to an extent of at least 90% by mass, especially to an extent of at least 95% by mass, this content figure being based on the metal component of the reduced catalyst only, excluding the support material component.

$R^2$ contains from 2 to 600 oxyalkylene groups. In the present context, oxyalkylene groups are understood to mean a unit of the formula —(AO)— in which A is a $C_2$- to $C_4$-alkylene group. From 2 to 600 oxyalkylene groups thus mean a structural unit of the formula —$(AO)_n$—where n=from 2 to 600.

In the oxyalkylene chain represented by $(A-O)_n$, A is preferably an ethylene radical —$CH_2$—$CH_2$— or a propylene radical —($CH_2$—$CH(CH_3)$)—, especially an ethylene radical. The total number of oxyalkylene units is preferably between 5 and 300, especially between 8 and 200. The oxyalkylene chain may be a block polymer chain which has alternating blocks of different oxyalkylene units, preferably oxyethylene and oxypropylene units. It may also be a chain having a random sequence of the oxyalkylene units, a chain having chain segments composed of blocks of different oxyalkylene units and having chain segments having a random sequence of the oxyalkylene units, or a homopolymer.

In a preferred embodiment, —$(A-O)_n$— is an oxyalkylene chain of the formula 4

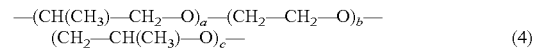

$$—(CH(CH_3)—CH_2—O)_a—(CH_2—CH_2—O)_b—(CH_2—CH(CH_3)—O)_c— \qquad (4)$$

in which
a is from 0 to 300, preferably from 2 to 80,
b is from 3 to 300, preferably from 3 to 200,
c is from 0 to 300, preferably from 2 to 80.

$R^1$ and $R^3$ are the same or different and are each hydrogen or an organic radical having from 1 to 400 carbon atoms. $R^1$ and $R^3$ may, as well as carbon and hydrogen, also contain heteroatoms such as oxygen, nitrogen, phosphorus or sulfur.

In a preferred embodiment, $R^1$ and $R^3$ are each hydrogen, an alkyl radical having from 1 to 50 carbon atoms, an alkylene radical having from 2 to 50 carbon atoms, an aryl radical having from 6 to 50 carbon atoms or an alkylaryl radical having from 7 to 50 carbon atoms.

In particular $R^1=R^3=H$

In a further preferred embodiment, $R^1$ and $R^3$ are each as defined for $R^2$.

In a further preferred embodiment, $R^1$ and $R^3$ each contain amino groups. $R^1$ and $R^3$ then correspond to the formula 5

$$(5)$$

in which $R^4$ is a divalent hydrocarbon group having from 1 to 50 carbon atoms and $R^5$ and $R^6$ may each be hydrogen or a monovalent hydrocarbon group having from 1 to 50 carbon atoms, where each of $R^4$, $R^5$ and $R^6$ may comprise from 1 to 200 oxyalkylene groups and heteroatoms such as oxygen, nitrogen, phosphorus or sulfur (basically in the same way as $R^3$), and m is from 1 to 10.

When $R^2$ is alkoxylated methanol, the product of the process according to the invention may, for example, have the following structures:

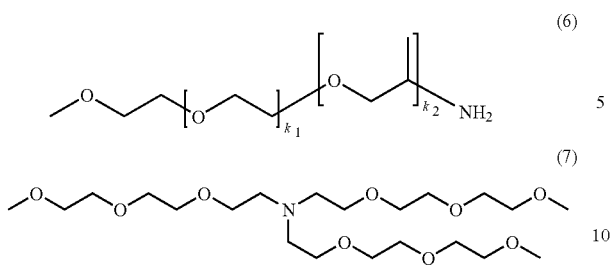

(6)

(7)

In the case of an alkoxylated alkyl alcohol, the following structure arises:

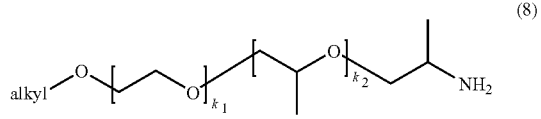

(8)

In the case of polyalkylene glycols (diols), the following structures arise:

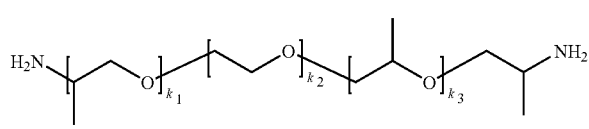

(9)

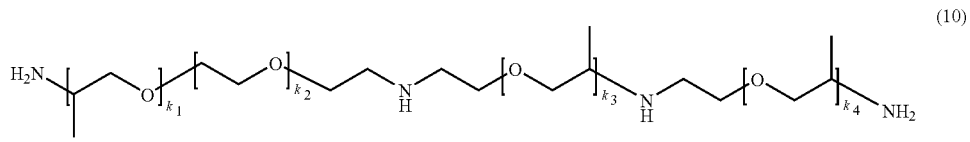

(10)

in which $k_1$, $k_2$, $k_3$ and $k_4$ are each integers which add up to 600.

In a further preferred embodiment, n is 1, 2, 3 or 4, and $R^2$ is an organic radical which has between 5 and 300 oxyalkylene groups.

In a further preferred embodiment, n is an integer from 5 to 20, and $R^2$ is an organic radical which contains from 2 to 300 oxyalkylene groups.

When $R^2$ is alkoxylated glycerol, the product of the process according to the invention may, for example, have the following structure:

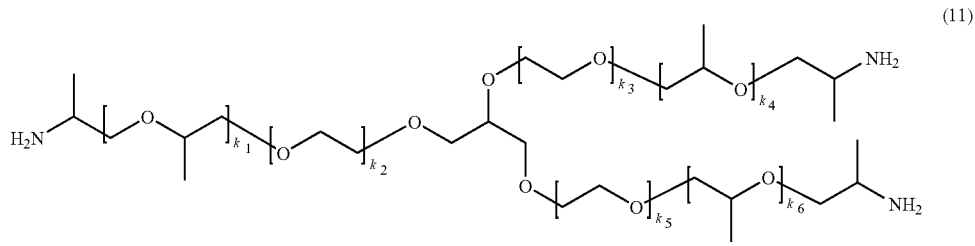

(11)

in which the indices $k_n$ are integers which add up to 600.

When $R^2$ is alkoxylated octylamine, the product of the process according to the invention may, for example, have the following structure:

(12)

in which the indices $k_n$ are integers which add up to 600.

Inventive polyetheramines are mono- or polyfunctional amines which may be branched, unbranched or cyclic, saturated or unsaturated. They may be primary, secondary or tertiary amines. Preference is given to primary amines where $R^1=R^2=H$.

Inventive polyetheramines are, for example, monofunctional amines, for example alkyl polyalkylene glycol amines, for example methyl triethylene glycol amine, bis(methyl triethylene glycol) amine, butyl triethylene glycol amine, lauryl polypropylene glycol amine, methyl tripropylene glycol amine, phenol polypropylene glycol amine, isotridecyl polypropylene glycol amine, bis(methyl tripropylene glycol) amine, N-methyl methyl polypropylene glycol amine, methyl polypropylene glycol amine, bis(methyl polypropylene glycol) amine, tris(methyl diglycol) amine, methyl polyalkylene glycol amine with random or blockwise distribution of the oxyethylene and oxypropylene units, difunctional amines, for example triethylene glycol diamine, tripropylene glycol diamine, polyethylene glycol diamine, polypropylene glycol diamine, polyalkylene glycol diamine with random or blockwise distribution of oxyethylene and oxypropylene units, butanediol polyalkylene glycol diamine, resorcinol polyalkylene glycol diamine, trifunctional amines, for example
glycerol polyalkylene glycol triamine with random or blockwise distribution of the oxyethylene and oxypropylene units, bis(triethylene glycol amine) amine, bis(polyalkylene glycol amine) amine,
tetrafunctional amines, for example
pentaerythritol polyalkylene glycol tetraamine with random or blockwise distribution of the oxyethylene and oxypropylene units, N,N'-bis(polypropylene glycol amine) polyalkylene glycol diamine.

The aminating agents of the formula (2) used in the amination of the polyether alcohols of the formula (3) to give the polyether amines of the formula (1) by the process according to the invention may be either ammonia or primary or secondary, aliphatic or cycloaliphatic or aromatic amines.

In the case of use of ammonia as the aminating agent, a primary polyether amine is initially formed. Under appropriate reaction conditions (pressure, temperature, reaction time, catalyst), this can be isolated as the product, or the reaction is continued such that the primary polyetheramine formed reacts further with further alcohol to give the corresponding secondary or else tertiary polyetheramine.

In addition to ammonia, the following amines, for example, can be used as aminating agents: methylamine, dimethylamine, ethylamine, diethylamine, n-propylamine, di-n-propylamine, isopropylamine, diisopropylamine, hexylamine, cyclohexylamine, aniline, toluidine, piperidine, morpholine.

The aminating agent may, based on the hydroxyl group to be aminated, be used in stoichiometric, substoichiometric or superstoichiometric amounts. If high conversions of the alcohol of the formula (3) are to be achieved, the aminating agent, for example ammonia, is preferably used in a molar excess and unconverted aminating agent is recovered. The partial hydrogen presssure to be used may likewise be varied within a wide range, for example from 1 bar to 60 bar, more particularly from 10 bar to 40 bar. Hydrogen is not consumed stoichiometrically but is required to maintain the catalyst activity.

The process according to the invention is performed preferably at temperatures of from 50 to 250° C., especially at temperatures of from 140° C. to 200° C. Continuous aminolysis processes are preferably carried out at temperatures from 140° C. to 200° C., particularly preferably at temperatures from 150° C. to 180° C., for example as a trickle-bed or bottom process. In the trickle-bed process, the compounds of the formula (3) are metered into the upright fixed bed reactor from the top, and in the bottom process they are metered from the bottom.

The process according to the invention is performed preferably at overall pressures of from 1 bar to 300 bar, in the case of ammonia or volatile aminating agents preferably at overall pressures of from 30 to 300 bar, especially from 50 bar to 200 bar.

The amount of catalyst to be used is preferably in the range from 0.5 to greater than 90% by mass, more particularly from 1 to 80% by mass, especially from 2 to 70% by mass, based on the alcohol of the formula (3) used. Amounts above 70% by mass are used especially in continuous processes in a fixed bed reactor. In batchwise processes, smaller amounts of catalyst in the range of from 2 to 15% by mass per batch are generally used, and the catalyst is recovered and then reused for a large number of batches.

The amination can be performed continuously, for example in fixed bed reactors, or batchwise, for example in stirred reactors or loop reactors. In both processes, the gaseous or in some cases even supercritical reaction components (aminating agent, hydrogen and possibly inert gases) can be circulated.

The water which forms during the reaction can either remain in the reaction mixture or else optionally be removed if the desired conversion otherwise suffers with regard to reaction rate, catalyst lifetime, yield and/or selectivity.

The amination is preferably performed without solvent. However, it is also possible to use solvents.

The resulting reaction effluent is freed of catalyst, of excess aminating agent, of water formed, of hydrogen and of optionally inert gases, and the polyetheramine is further purified appropriately according to the requirement. The reaction components removed may, possibly after appropriate workup, be sent back to the amination process. The catalyst is reused without loss of activity or selectivity.

EXAMPLES

Example 1

1.0 kg of methyl polyalkylene glycol with a mean molar mass of 2000 g/mol, 200 g of a Raney catalyst which had been freed of water under protective nitrogen gas, and 600 ml of ammonia (liquid) were introduced into an agitated autoclave of capacity 4.5, 1 equipped with a catalyst basket. The Raney catalyst was in the form of porous hollow spheres of external diameter 3 mm and consisted of 64% by mass of cobalt and 32% by mass of aluminum, based on the metal content in the dry state. The copper content, based on the metal content in the dry state, was 0.2% by mass. Subsequently, 30 bar hydrogen were injected and the autoclave was closed. The mixture was heated to 180° C. while being agitated for 20 hours.

The overall pressure at 180° C. was about 160 bar. After cooling to 50° C., the autoclave was slowly decompressed in order to remove the majority of the ammonia and the hydrogen. The remaining reaction mixture was freed under reduced pressure of residual volatile constituents such as ammonia and water of reaction formed and filtered. The determination of the amine number and the hydroxyl number allowed a degree of conversion of 94% to the corresponding polyetheramine to be determined. The selectivity for the primary polyetheramines determined by titrimetry was 98 equivalent %, based on the total amine content.

To determine the selectivities, the distributions of the primary, secondary and tertiary polyetheramines were determined by masking reactions with acetic anhydride or salicylaldehyde and in each case subsequent acid-base titrations. In addition the polyetheramines and the samples derivatized with trichloroacetyl isocyanate were analyzed by 1H NMR spectroscopy.

Example 2

1.0 kg of methyl polyalkylene glycol with a mean molar mass of 2000 g/mol, 130 g of a supported catalyst which had been reduced with hydrogen and activated beforehand, and 600 ml of ammonia (liquid) were introduced into an agitated autoclave of capacity 4.5 l, equipped with a catalyst basket. The reduced supported catalyst was in the form of rods about 3 mm in length and consisted of the support material aluminum oxide to an extent of 90% by mass and of metals to an extent of 10% by mass, the proportion of the cobalt, based on the metal content excluding the aluminum oxide support material, having been more than 98% by mass and the proportion of the copper, based on the metal content excluding the aluminum oxide support material, having been 0.4% by mass. Subsequently, 30 bar hydrogen were injected and the autoclave was closed. The mixture was heated to 180° C. while being agitated for 5 hours. The overall pressure at 180° C. was about 160 bar. After cooling to 50° C., the autoclave was slowly decompressed in order to remove the majority of the ammonia and the hydrogen. The remaining reaction mixture was freed under reduced pressure of residual volatile constituents such as ammonia and water of reaction formed and filtered. The determination of the amine number and hydroxyl number allowed a degree of conversion of 97% to the corresponding polyetheramine to be determined. The selectivity for the primary polyetheramines determined by titrimetry was 99 equivalent %, based on the total amine content.

Example 3

1.0 kg of methyl polyalkylene glycol with a mean molar mass of 2000 g/mol, 200 g of a supported catalyst whose metal content, based on the dry, reduced catalyst excluding the $SiO_2$/MgO, support material, consisted of cobalt to an extent of more than 95% by mass and of copper to an extent of 0.8% by mass, and 540 ml of ammonia (liquid) were metered into a stirred autoclave of capacity 2 l. Subsequently, 30 bar hydrogen were injected and the autoclave was closed. The mixture was heated to 190° C. while being stirred for 7 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding polyetheramine to be determined. The selectivity for the primary polyetheramines, determined by titrimetry, was 98 equivalent %, based on the total amine content.

Example 4

1.0 kg of methyl polyalkylene glycol with a mean molar mass of 2000 g/mol, 180 g of pulverulent cobalt catalyst of the Raney type, whose total content of cobalt and aluminum, based on the anhydrous catalyst, was 94% by mass and whose copper content was less than 0.2% by mass, and 540 ml of ammonia (liquid) were metered into a stirred autoclave of capacity 2 l. Subsequently, 10 bar hydrogen were injected and the autoclave was closed. The mixture was heated to 190° C. while being stirred for 6 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding polyetheramine to be determined. The selectivity for the primary polyetheramines, determined by titrimetry, was 97 equivalent %, based on the total amine content.

Example 5

750 g of polyalkylene glycol consisting of ethylene glycol and propylene glycol units and having a mean molar mass of 600 g/mol, 150 g of a supported catalyst whose metal content, based on the dry, reduced catalyst excluding the $SiO_2$ support material, consisted of cobalt to an extent of 98% by mass and of copper to an extent of 0.3% by mass, and 800 ml of ammonia (liquid) were metered into a stirred autoclave of capacity 4.5 l. Subsequently, 10 bar hydrogen were injected and the autoclave was closed. The mixture was heated to 190° C. while being agitated for 6 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding polyetherdiamine to be determined. The selectivity for the primary polyetheramines, determined by titrimetry, was 96 equivalent %, based on the total amine content.

Example 6

1.0 kg of polyalkylene glycol consisting of ethylene glycol and propylene glycol units and having a mean molar mass of 4000 g/mol, 200 g of a supported catalyst whose metal content, based on the dry, reduced catalyst excluding the $SiO_2$ support material, consisted of cobalt to an extent of 93% by mass and of copper to an extent of 1.2% by mass, and 540 ml of ammonia (liquid) were metered into a stirred autoclave of capacity 2 l. Subsequently, 10 bar hydrogen were injected and the autoclave was closed. The mixture was heated to 190° C. while being stirred for 5 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding polyetheramine to be determined. The selectivity for the primary polyetheramines, determined by titrimetry was 98 equivalent %, based on the total amine content.

Example 7

1.5 kg of methyl polyalkylene glycol with a mean molar mass of 2000 g/mol, 100 g of cobalt catalyst of the Raney type, whose total content of cobalt and aluminum, based on the anhydrous catalyst, was 91% by mass, and 800 ml of ammonia (liquid) were metered into an agitated autoclave of capacity 4.5 l. Subsequently, 10 bar hydrogen were injected and the autoclave was closed. The mixture was heated to 190° C. while being agitated for 12 hours, an overall pressure of 180 bar being maintained by injecting further hydrogen. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 85% to the corresponding polyetheramine to be determined. The selectivity for the primary polyetheramines, determined by titrimetry, was 98 equivalent %, based on the total amine content.

Example 8

1.0 kg of fatty alcohol oxypropylate with a mean molar mass of 310 g/mol, 200 g of a supported catalyst whose metal content, based on the dry, reduced catalyst excluding the support material, consisted of cobalt to an extent of 94% by mass and of copper to an extent of 0.2% by mass, and 540 ml of ammonia (liquid) were metered into a stirred autoclave of capacity 2 l. Subsequently, 5 bar hydrogen were injected and the autoclave was closed. The mixture was heated to 190° C. while being stirred for 8 hours. The water of reaction formed remained in the stirred autoclave. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 80% to the primary amine to be determined. No content of secondary and tertiary amines was detectable.

Example 9

1.0 kg of fatty alcohol oxypropylate with a mean molar mass of 310 g/mol, 50 g of a supported catalyst whose metal content, based on the dry, reduced catalyst excluding the support material, consisted of cobalt to an extent of 94% by mass and of copper to an extent of 0.2% by mass, and 540 ml of ammonia (liquid) were metered into a stirred autoclave of capacity 2 l. Subsequently, 5 bar hydrogen were injected and the autoclave was closed. The mixture was heated to 190° C. while being stirred for 24 hours. The water of reaction formed remained in the autoclave. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 75% to the corresponding primary amine to be determined. The content of secondary and tertiary amines was <1 mol %.

Example 10

A fixed bed reactor having a diameter of 5 cm and a length of 2.5 m was charged with tablets of a supported catalyst whose metal content, based on the dry, reduced catalyst excluding the SiO$_2$/MgO support material, consisted of cobalt to an extent of 96% by mass and of copper to an extent of 0.3% by mass, and the catalyst was activated under reductive conditions with hydrogen. Subsequently, 1 kg/h of fatty alcohol propoxylate having a mean molar mass of 310 g/mol, 2.5 kg/h of ammonia and hydrogen were fed into the reactor at a temperature of 160° C. and an overall pressure of 100 bar. The reactor was operated in cycle gas mode, and the water of reaction formed was removed with an offgas stream. Once stable reaction conditions had been established in the reactor, samples of the product effluent were taken and any ammonia and water still dissolved in the samples were removed under reduced pressure. The determination of the amine number and the hydroxyl number allowed a conversion of 98% to be determined. The selectivity for the primary amines, determined by titrimetry, was 98 equivalent %, based on the total amine content.

Example 11

As described in Example 10, a fixed bed reactor was charged with catalyst and conditioned. Subsequently, 1 kg/h of fatty alcohol propoxylate having a mean molar mass of 310 g/mol, 2.5 kg/h of ammonia and hydrogen were fed into the reactor at a temperature of 155° C. and an overall pressure of 90 bar. Once stable reaction conditions had been established in the reactor, samples of the product effluent were taken. The water of reaction formed remained in the autoclave. The determination of the amine number and the hydroxyl number allowed a conversion of 96% to be determined. The selectivity for the primary polyetheramines, determined by titrimetry, was 99 equivalent %, based on the total amine content.

Example 12

As described in Example 10, a fixed bed reactor was charged with catalyst and conditioned. Subsequently, 1 kg/h of methyl polyalkylene glycol having a mean molar mass of 2000 g/mol, 5 kg/h of ammonia and hydrogen were fed into the reactor at a temperature of 160° C. and an overall pressure of 50 bar. Once stable reaction conditions had been established, samples of the product effluent were taken and ammonia and water still dissolved in the samples were removed under reduced pressure. The determination of the amine number and the hydroxyl number allowed a conversion of 90% to be determined. The selectivity for the primary polyetheramines, determined by titrimetry, was 98 equivalent %, based on the total amine content.

Example 13 (Comparative Example)

1.0 kg of methyl polyalkylene glycol with a mean molar mass of 2000 g/mol, 130 g of a supported catalyst which had been reduced with hydrogen and activated beforehand, and 600 ml of ammonia (liquid) were introduced into an agitated autoclave of capacity 4.5 l, equipped with a catalyst basket. The reduced supported catalyst was in the form of rods about 3 mm in length and consisted of the support material aluminum oxide to an extent of 89% by mass and of metals to an extent of 11% by mass, the proportion of the cobalt, based on the metal content excluding the aluminum oxide support material, having been 87% by mass and the proportion of the copper, based on the metal content excluding the aluminum oxide support material, having been 12% by mass. Subsequently, 30 bar hydrogen were injected and the autoclave was closed. The mixture was heated to 180° C. while being agitated for 5 hours. The overall pressure at 180° C. was about 160 bar. After cooling to 50° C., the autoclave was slowly decompressed in order to remove the majority of the ammonia and the hydrogen. The remaining reaction mixture was freed under reduced pressure of residual volatile constituents such as ammonia and water of reaction formed and filtered. The determination of the amine number and hydroxyl number allowed a degree of conversion of 88% to the corresponding polyetheramine to be determined. The selectivity for the primary polyetheramines, determined by titrimetry, was 91 equivalent %, based on the total amine content. In addition, 8 equivalent % of secondary polyetheramines and 1 equivalent % of tertiary polyetheramines, based on the total amine content, were found.

The invention claimed is:

1. A process for preparing an amine of the formula I

wherein n is a number from 1 to 20, $R^2$ is an organic radical which comprises between 2 and 600 oxyalkylene groups, and $R^1$ and $R^3$ are the same or different and are each hydrogen or an organic radical having from 1 to 400 carbon atoms, comprising the step of combining a compound of the formula 2

with a compound of the formula 3

in the presence of hydrogen with a catalyst which is metallic and whose metal content, based on the dry, reduced catalyst excluding any support material present, either is at least 80% cobalt by mass or, in the case of the Raney catalysts is at least 80% cobalt and aluminum by mass, and which contains less than 5% by mass of copper.

2. The process as claimed in claim 1, wherein $R^1$ and $R^3$ are each selected from the group consisting of: hydrogen, an alkyl radical having from 1 to 50 carbon atoms, an alkylene radical having from 2 to 50 carbon atoms, an aryl radical having from 6 to 50 carbon atoms, and an alkylaryl radical having from 7 to 50 carbon atoms.

3. The process as claimed in claim 1, wherein $R^1$ and $R^3$ are each as defined for $R^2$.

4. The process as claimed in claim 1, wherein $R^1$ and $R^3$ each contain an amino group.

5. The process as claimed in claim 1, wherein $R^1$ and $R^3$ each correspond to the formula 5

wherein $R^4$ is a divalent hydrocarbon group having from 1 to 50 carbon atoms and $R^5$ and $R^6$ may each be hydrogen or a monovalent hydrocarbon group having from 1 to 50 carbon atoms, where each of $R^4$, $R^5$ and $R^6$ may comprise from 1 to 200 oxyalkylene groups, and m is from 1 to 10.

6. The process as claimed in claim 1, wherein n is 1, 2, 3 or 4, and wherein $R^2$ is an organic radical which has between 5 and 300 oxyalkylene groups.

7. The process as claimed in claim 1, wherein n is an integer from 5 to 20, and wherein $R^2$ is an organic radical which has from 2 to 300 oxyalkylene groups.

8. The process as claimed in claim 1, wherein $R^1$ and $R^3$ are each hydrogen.

9. The process as claimed in claim 1, wherein the catalyst contains at least 90% by mass of cobalt and the percentages by mass are based on the dry, reduced catalyst excluding support material.

10. The process as claimed in claim 1, wherein the catalyst of the Raney cobalt type contains at least 90% by mass of metal, wherein the metal is selected from the group consisting of cobalt and aluminum and the percentages by mass are based on the dry catalyst.

11. The process as claimed in claim 1, wherein the catalyst contains between less than 5 and 0.1% by mass of copper.

12. The process as claimed in claim 1, wherein the catalyst contains less than 4% by mass of copper.

13. The process as claimed in claim 1, wherein n is one or two.

14. The process as claimed in claim 1, wherein the reaction temperature is from 50 to 250° C.

15. The process as claimed in claim 1, wherein the overall pressure is from 1 to 300 bar.

16. The process as claimed in claim 1, wherein the process is carried out continuously in a fixed bed reactor.

* * * * *